United States Patent
Lauryssen et al.

(10) Patent No.: US 8,491,643 B2
(45) Date of Patent: Jul. 23, 2013

(54) ANTERIOR BONE PLATE SYSTEM AND METHOD OF USE

(75) Inventors: Carl Lauryssen, Malibu, CA (US); Morris Cesarone, Linwood, MA (US); Dennis Cirino, Lincoln, MA (US); Danielle Sheeran, Westwood, MA (US)

(73) Assignee: DePuy Spine, Inc., Raynham, MA (US)

( * ) Notice: Subject to any disclaimer, the term of this patent is extended or adjusted under 35 U.S.C. 154(b) by 1497 days.

(21) Appl. No.: 10/908,008

(22) Filed: Apr. 25, 2005

(65) Prior Publication Data
US 2005/0182404 A1 Aug. 18, 2005

Related U.S. Application Data

(63) Continuation of application No. 10/108,249, filed on Mar. 27, 2002, now abandoned.

(51) Int. Cl.
*A61B 17/80* (2006.01)

(52) U.S. Cl.
USPC .............................................. 606/280

(58) Field of Classification Search
USPC .................... 606/69–71; 403/61, 71
See application file for complete search history.

(56) References Cited

U.S. PATENT DOCUMENTS

| | | | |
|---|---|---|---|
| 1,025,008 A | 4/1912 | Miner | |
| 4,388,921 A | 6/1983 | Sutter et al. | |
| 4,524,765 A * | 6/1985 | de Zbikowski | 606/280 |
| 4,696,290 A | 9/1987 | Steffee | |
| 4,943,292 A | 7/1990 | Foux | |
| 5,057,111 A | 10/1991 | Park | |
| 5,085,660 A | 2/1992 | Lin | |
| 5,129,899 A | 7/1992 | Small et al. | |
| 5,180,381 A | 1/1993 | Aust | |
| 5,234,431 A | 8/1993 | Keller | |
| 5,261,910 A | 11/1993 | Warden et al. | |
| 5,290,288 A | 3/1994 | Vignaud et al. | |
| 5,344,421 A | 9/1994 | Crook | |
| 5,423,826 A | 6/1995 | Coates et al. | |
| 5,486,176 A | 1/1996 | Hildebrand et al. | |
| 5,501,684 A | 3/1996 | Schlapfer et al. | |
| 5,514,138 A | 5/1996 | McCarthy | |

(Continued)

FOREIGN PATENT DOCUMENTS

| | | |
|---|---|---|
| WO | WO 96/05778 | 2/1996 |
| WO | WO 03/007826 | 1/2003 |
| WO | WO 03-024344 | 3/2003 |

OTHER PUBLICATIONS

DePuy Acromed (now DePuy Spine); Summit Fixation System product catalog, 1999.

(Continued)

*Primary Examiner* — Eduardo C Robert
*Assistant Examiner* — David Comstock
(74) *Attorney, Agent, or Firm* — Nutter McClennen & Fish LLP

(57) ABSTRACT

An anterior bone plate system is provided that promotes osseous fusion and allows subsidence while restricting extension. The bone plate system requires a minimum number of screws for securing the plate onto bone, thus reducing the amount of osseous tissue damage incurred by the bone structures to which they are attached. The system is also simple to use and provides for independent screw placement while incurring minimal soft tissue damage from lateral retraction. A method for implementing the system is also provided.

10 Claims, 10 Drawing Sheets

U.S. PATENT DOCUMENTS

| | | | |
|---|---|---|---|
| 5,549,612 A | 8/1996 | Yapp et al. | |
| 5,584,887 A | 12/1996 | Kambin | |
| 5,603,713 A | 2/1997 | Aust | |
| 5,616,144 A * | 4/1997 | Yapp et al. | 606/61 |
| 5,676,666 A | 10/1997 | Oxland et al. | |
| 5,716,357 A | 2/1998 | Rogozinski | |
| 5,728,127 A | 3/1998 | Asher et al. | |
| 5,733,287 A | 3/1998 | Tepic et al. | |
| 5,735,850 A | 4/1998 | Baumgartner et al. | |
| 5,851,207 A | 12/1998 | Cesarone | |
| 5,976,139 A | 11/1999 | Bramlet | |
| 6,017,345 A | 1/2000 | Richelsoph | |
| 6,129,730 A * | 10/2000 | Bono et al. | 606/73 |
| 6,139,550 A | 10/2000 | Michelson | |
| 6,152,927 A | 11/2000 | Farris et al. | |
| 6,159,213 A | 12/2000 | Rogozinski | |
| 6,224,602 B1 | 5/2001 | Hayes | |
| 6,235,034 B1 | 5/2001 | Bray | |
| 6,261,291 B1 | 7/2001 | Talaber et al. | |
| 6,280,445 B1 | 8/2001 | Morrison et al. | |
| 6,287,309 B1 | 9/2001 | Baccelli et al. | |
| 6,302,883 B1 | 10/2001 | Bono | |
| 6,342,057 B1 | 1/2002 | Brace et al. | |
| 6,350,265 B1 | 2/2002 | Blaustein et al. | |
| 6,379,364 B1 | 4/2002 | Brace et al. | |
| 6,413,259 B1 | 7/2002 | Lyons et al. | |
| 6,565,571 B1 | 5/2003 | Jackowski | |
| 6,641,583 B2 | 11/2003 | Shluzas et al. | |
| 6,695,844 B2 | 2/2004 | Bramlet et al. | |
| 7,063,701 B2 * | 6/2006 | Michelson | 606/307 |
| 2001/0047172 A1 | 11/2001 | Foley et al. | |
| 2002/0065517 A1 | 5/2002 | Paul | |
| 2002/0082606 A1 | 6/2002 | Suddaby | |
| 2002/0128654 A1 | 9/2002 | Steger et al. | |
| 2003/0036759 A1 | 2/2003 | Musso | |
| 2003/0233098 A1 | 12/2003 | Markworth | |
| 2004/0015174 A1 | 1/2004 | Null | |
| 2004/0092947 A1 | 5/2004 | Foley | |

OTHER PUBLICATIONS

DePuy Acromed (now DePuy Spine); engineering drawing of an Anterior Cervical Buttress Plate; the plate was first shipped on Jul. 12, 2000.

Spinetech, Inc.; Cervi-Lok Cervical Fixation System, Surgical Technique Manual.

* cited by examiner

ANTERIOR BONE PLATE SYSTEM AND METHOD OF USE

CROSS REFERENCE TO RELATED APPLICATIONS

This application is a continuation of application Ser. No. 10/108,249 filed Mar. 27, 2002, which is hereby incorporated by reference in its entirety.

FIELD OF THE INVENTION

The present invention relates to fixation devices used in orthopedic and spinal surgery and particularly to bone fixation plates useful for positioning and immobilizing bone segments.

BACKGROUND OF THE INVENTION

For a number of known reasons, bone fixation devices are useful for promoting proper healing of injured or damaged vertebral bone segments caused by trauma, tumor growth, or degenerative disc disease. The external fixation devices immobilize the injured bone segments to ensure the proper growth of new osseous tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is an osteosynthesis plate, more commonly referred to as a bone fixation plate, that can be used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

Such plates have been used to immobilize a variety of bones, including vertebral bodies of the spine. These bone plate systems usually include a rigid bone plate having a plurality of screw openings. The openings are either holes or slots to allow for freedom of screw movement. The bone plate is placed against the damaged vertebral bodies and bone screws are used to secure the bone plate to the spine, usually with the bone screws being driven into the vertebral bodies. Exemplary systems like the one just described can be found in U.S. Pat. No. 6,159,213 to Rogozinski, U.S. Pat. No. 6,017,345 to Richelsoph, U.S. Pat. No. 5,676,666 to Oxiand et al., U.S. Pat. No. 5,616,144 to Yapp et al., U.S. Pat. No. 5,549,612 to Yapp et al., U.S. Pat. No. 5,261,910 to Warden et al., and U.S. Pat. No. 4,696,290 to Steffee.

Despite the existence of these bone plate systems, there remains a need for an anterior bone plate system that minimizes any soft tissue and osseous tissue damage that would occur with its implementation and still be easy to use. The system must be able to provide effective fixation and immobilization of vertebral bodies, while also providing for the subsidence necessary for proper fusion and prevent axial extension of the plate.

BRIEF SUMMARY OF THE INVENTION

The present invention achieves the aforementioned goals by providing an anterior bone plate system that promotes osseous fusion and allows subsidence while restricting extension. The bone plate system further requires a minimum number of screws for securing the plate onto bone, thus reducing the amount of osseous tissue damage incurred by the bone structures to which they are attached. The system is also simple to use and provides for independent screw placement while incurring minimal soft tissue damage from lateral retraction.

These desired features are accomplished by providing a system comprising a bone plate having a first surface, a second bone-contacting surface opposed to the first surface, and a channel formed on the first surface extending lengthwise from one end of the plate to an opposite end. A plurality of apertures extend through the channel. Each aperture has a predefined shape and size. A plurality of screws capable of insertion into bone are also provided. Each screw has a lower threaded portion at one end and an open screw head at an opposite end. The screw head has a complementary shape and size sufficient to pass through the apertures of the bone plate. Also included is a locking mechanism for securing the bone plate onto the screws.

According to one aspect of the invention, the aperture and the screw head is oblong in shape. The bone plate can also include surface features such as cleats on the bone-contacting surface. The bone plate can further include a rigid flap or lip on each side of the plate extending lengthwise from one end of the plate to the opposite end. The flaps can extend over the channel.

In one exemplary embodiment of the present invention, each screw has a self-tapping end extending from the lower threaded portion. Further, each screw head can extend into an upper threaded portion configured to sit proud, i.e., not engaged in bone. A locking device can be provided to secure the bone plate onto the screws. The locking device can be a nut, cam, wedge, or a retaining ring.

In another exemplary embodiment of the present invention, each flap includes a notched region, and each screw head includes a pair of diametrically opposed ramps. Each of the ramps further includes a groove for engagement with the notched region of the flaps. In this system, the bone plate can be effectively locked onto the screws by placing the plate over the screws and rotating the screw heads 90 degrees so that the grooves of the ramps and the notched regions of the flaps form an interference fit.

Also provided is a method for stabilizing and rigidly fixing vertebral bodies in a patient, involving the steps of identifying a damaged region of the patient's spine, preparing a pilot hole in each of the vertebral bodies in the damaged region, removing osteophytes from the selected vertebral bodies, creating a smooth flat surface on the selected vertebral bodies, providing an anterior bone plate system as described above, inserting a screw in each of the pilot holes, placing the bone plate over the screws, and locking the bone plate to the screws.

The pilot holes can be prepared by inserting a distraction pin into each of the selected vertebral bodies. Each of the distraction pins should be inserted in the midline of the vertebral bodies, with only one pilot hole being made in each vertebral body. Hence, only one screw is inserted into any single vertebral body, reducing the osseous damage to the spine.

If necessary, the selected vertebral bodies can be distracted and a diseased disc removed from the damaged region. A graft can then be placed into the evacuated disc space. Prior to inserting the screws and plate, the vertebral bodies must be shaved to create a smooth flat surface that precisely matches the width of the bone plate. This ensures proper adhesion of the plate to the bony surface and also produces a low profile so that damage to surrounding soft tissue can be minimized.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying drawings, in which.

DETAILED DESCRIPTION OF THE INVENTION

The present invention provides an anterior bone plate system which is easy to use and allows independent screw placement. The system requires only one bone screw to be used per vertebral body level, thus reducing the amount of osseous tissue damage to the vertebral bodies. The bone plate system of the present invention also promotes good bone fusion by providing enough subsidence to facilitate proper bone growth, while at the same time preventing extension. Furthermore, the bone plate system of the present invention provides a good bone screw to plate interface locking mechanism.

Figure 1:
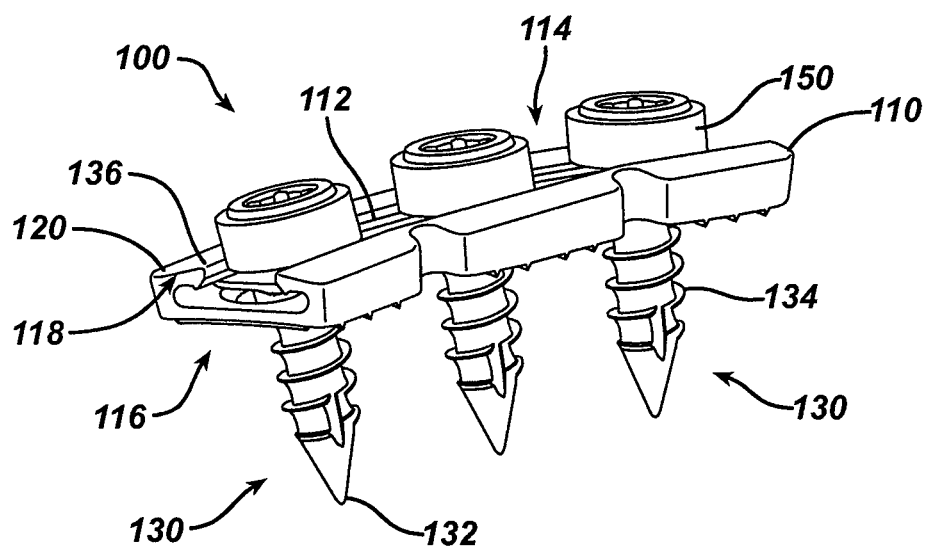
FIG. 1 is a perspective view of an anterior bone plate system of the present invention, wherein the screws are extending through the bone plate.
Figure 2:
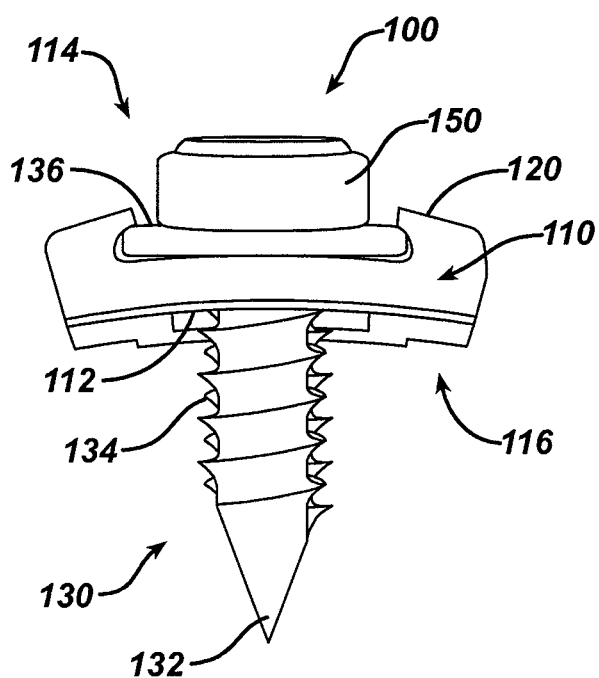
FIG. 2 is a side view of the system of FIG. 1.

Referring to FIG. 1, in one exemplary embodiment of the anterior bone plate system 100 of the present invention, a bone plate 110 with a plurality of screws 130 extending through apertures or slots 112 thereon are shown. The apertures 112 allow the plate 110 to be placed from above onto previously placed screws 130, thereby enabling independent screw placement. Each screw 130 has a self-tapping distal end 132 extending into a lower threaded portion 134 with an aggressive thread pitch to facilitate its purchase into bone. As shown in FIG. 2, each screw 130 includes a screw head 136 at an opposite (proximal) end that is adapted to seat within a channel 118 extending lengthwise on a first side 114 of the plate 110 that is configured to face away from a bony surface. Channel 118 is machined parallel to the longitudinal axis of the plate 110 such that a rigid lip or flap 120 is formed lengthwise on both sides of the bone plate 110. Each lip or flap 120 extends over a portion of the channel 118 as illustrated in FIGS. 1 and 2. Since the system 100 is a top loading plate system, this lip 120 ensures the proper placement of the bone plate 110 with respect to the screws 130 when the plate 110 is dropped down onto the screws 130.

In the present invention, screws 130 can have open screw heads 136. Each screw 130 can also include an upper threaded portion with threads set proud, i.e., not engaged in bone, for engaging a locking device such as a nut 150 as shown in FIG. 2. While a nut 150 has been illustrated, it is contemplated that other suitable locking devices such as a wedge, cam, or retaining ring can also be used. The major thread diameter of the lower threaded portion 134 of the screws 130 can be in the range of about 3.5 to 5.5 mm, while the cancellous thread pitch of the lower threaded region 134 can be approximately 1.5 or more to provide unicortical purchase into bone. The bone screws 130 are placed in the midline of the vertebral body, with only one bone screw 130 per vertebral body or level required to adequately stabilize the bone segments to the plate 110. This advantageous feature of the present invention reduces the amount of bone damage that would occur to the spine when more than one screw is inserted within the same vertebral body.

Figure 3:
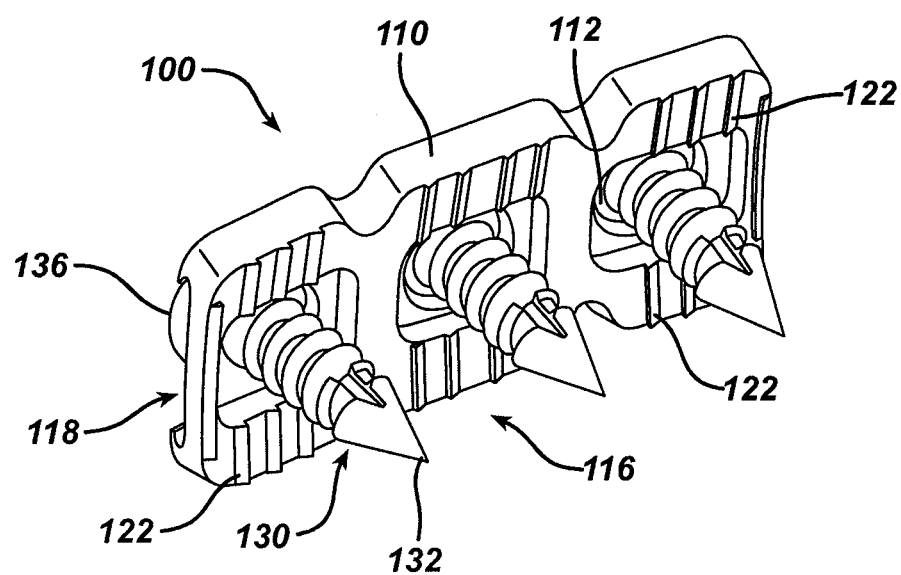
FIG. 3 is a perspective view showing the bottom of the system of FIG. 1.

Bone plate 110 can also include surface features 122 such as cleats or ridges on the second side 116 that is configured to contact bony surface as illustrated in FIG. 3. The surface features 122 help anchor the bone plate 110 onto the bony surface of the vertebral bodies yet still allow flexion or subsidence while preventing extension, which is undesirable for proper fusion and healing. As can be seen in FIG. 3, the apertures 112 of the bone plate 110 can be oblong in shape and extend in a lengthwise direction. Further, the screw heads 136 of each of the screws 130 can be oblong in shape, enabling them to pass through the apertures 112. Thus, it may be necessary to align the screws 130 unidirectionally, i.e., the oblong-shaped screw heads 136 are aligned lengthwise, so that the plate 110 can be placed on top of the screws 130.

The anterior bone plate system 100 can be configured such that the bone plate 110 is able to slide with respect to the screw heads 136 to allow for dynamic interaction with the bone segments. As is well understood and established by Wolff's Law, the ability of the plate 110 to distribute physiologic loads to the bone is important for the fusion process. Since osseous tissue grows along lines of stress, this translational characteristic acts to maintain compressive loads across the bone/graft interface to promote bony fusion. The ability of the bone plate 110 of the present invention to effect subsidence, particularly as a result of its oblong shaped apertures 212 that allow the plate 110 some micromotion relative to the screw heads 236, provides for effective fusion of bony segments.

While the plate 110 has been illustrated as having three apertures 112, it is contemplated that the bone plate 110 of the present invention should have at least two apertures 112 for immobilizing at least two bone segments. The plate 110 may also contain more than two or three apertures 112. Further, while the apertures 112 and screw heads 136 have been described as having an oblong shape, it is understood that the apertures 112 and screw heads 136 can have any complementary size, shape or geometry.

Figure 4:
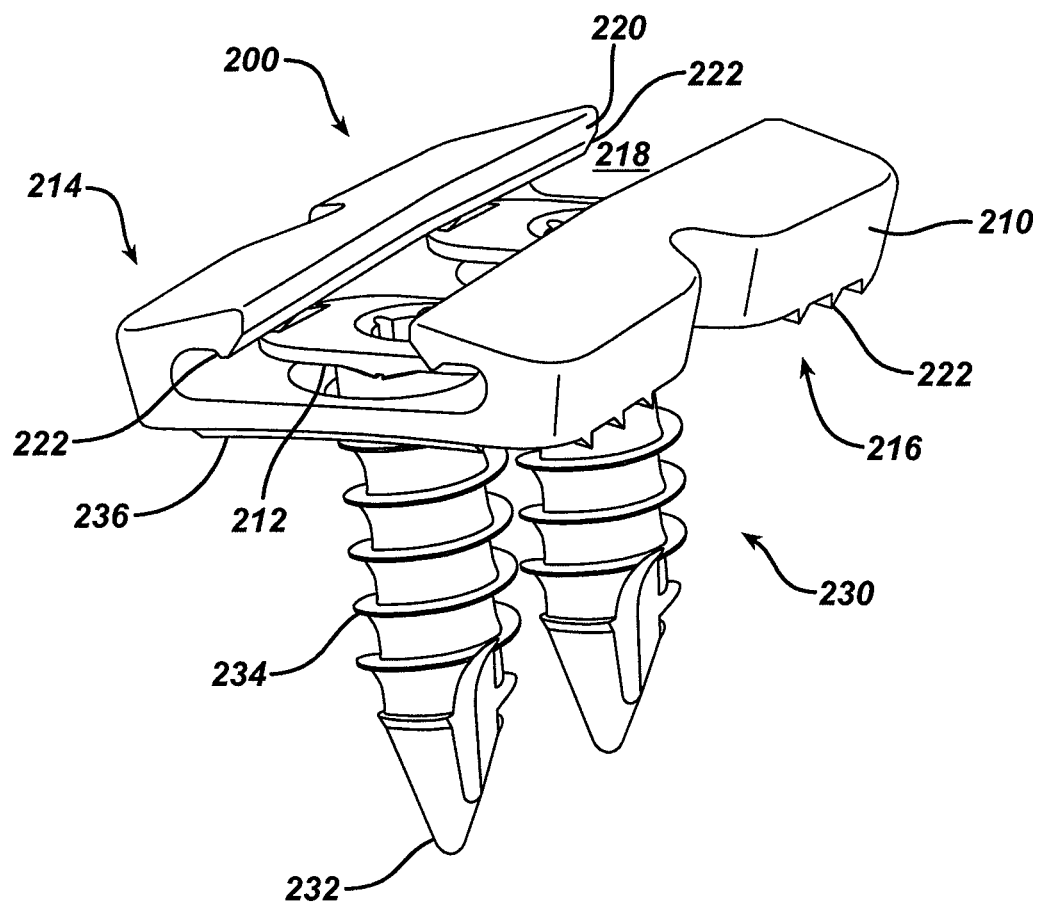
FIG. 4 is a perspective view of another embodiment of the anterior bone plate system of the present invention, wherein the screws are extending through the bone plate.
Figure 5:
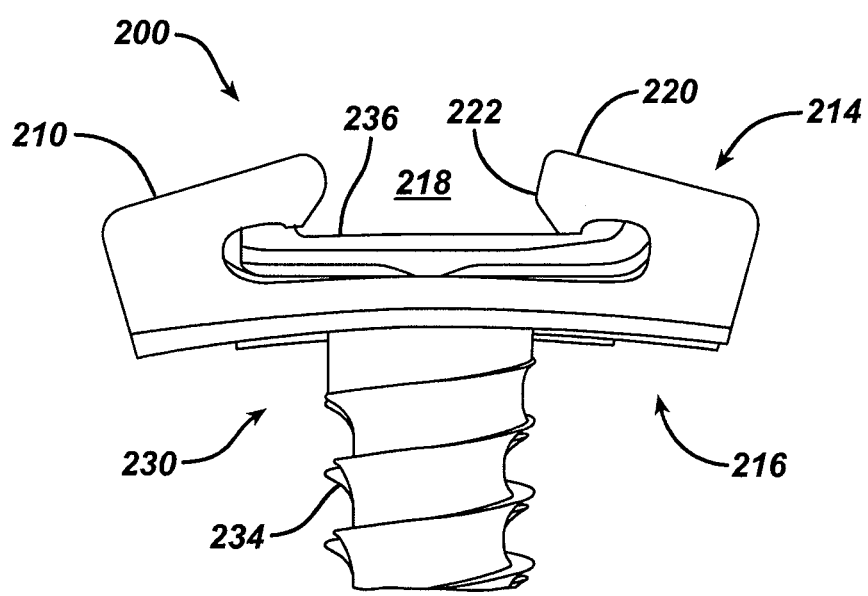
FIG. 5 is a side view of the system of FIG. 4.

In another exemplary embodiment of the present invention, FIG. 4 illustrates an anterior bone plate system 200 which provides an additional benefit in that it does not require additional external components to secure the bone plate 210 to screws 230. As shown in FIG. 4, bone plate 210 includes at least two apertures 212 extending from a first side 214 of the plate 210 that is configured to face away from bony structure to a second side 216 that is configured to contact bony surface. A channel 218 extends lengthwise down the first side 214 of the bone plate 210 and is machined parallel to the longitudinal axis of the plate 110 such that a rigid lip or flap 220 is created on both sides of the bone plate 210. Each lip or flap 220 runs lengthwise and extends over at least a portion of channel 218 as illustrated in FIGS. 4 and 5.

Figure 6:
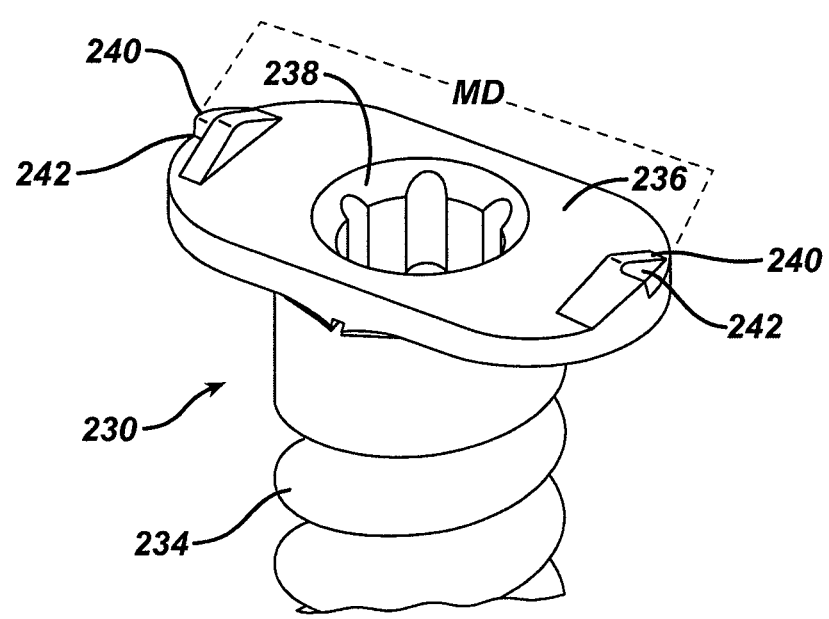
FIG. 6 is a detailed view of a portion of the screw of FIGS. 4 and 5.

Consistent with anterior bone plate system 100, the apertures 212 of bone plate 210 allow the plate 210 to be placed on top of previously placed bone screws 230. Each bone screw 230 can have a self-tapping distal end 232 extending into a lower threaded portion 234 with an aggressive thread pitch to facilitate its purchase into bone. As shown in FIG. 6, each screw 230 includes a screw head 236 at an opposite (proximal) end that is adapted to seat within the channel 218. The major thread diameter of the lower threaded portion 234 of screw 230 can be in the range of about 3.5 to 5.5 mm, while the cancellous thread pitch of the lower threaded region 234 can be approximately 1.5 or more to provide unicortical purchase into bone. The bone screws 230 are placed in the midline of the vertebral body, with only one bone screw 230 per vertebral body or level required to adequately stabilize the bony segments to the plate 210. This advantageous feature of the invention reduces the amount of bone damage that would occur to the spine when more than one screw is inserted within the same vertebral body.

Bone plate 210 can also include surface features 222 such as cleats or ridges on the second side 216 that is adapted to contact bony surface as illustrated in FIG. 4. The surface features 222 help anchor the bone plate 210 onto the bony surface of the vertebral bodies yet still allow flexion or subsidence while preventing extension, which is undesirable for proper fusion and healing.

As shown in FIG. 6, the screw heads 236 of each of the screws 230 can be oblong in shape, while the apertures 212 of bone plate 210 are also oblong in shape in a lengthwise direction so that the bone plate 210 can be placed on top of and pass through the screw heads 236 when the screws 230 are unidirectional, i.e., the oblong-shaped screw heads 236 are aligned lengthwise. Each screw 230 can also have an open head 236, which can include a shaped bore 238 for attachment to an inserter tool or screwdriver (not shown).

Extending proximally from the screw head 236, away from the self-tapping distal end 232, are a pair of diametrically opposed ramps 240. The ramps 240 are bi-level and include a cutaway portion, or groove 242 that is configured to frictionally engage with a notched region 222 on flaps 220 when the screws 230 are rotated 90°, i.e., rotated such that the major diameter MD of the screw head 236 is transversely oriented with respect to the long axis of plate 210. The complementary surface features on the screw heads 236 and flaps 220 provide a simple and effective locking mechanism for securing the plate 210 to the bony surface, without the need for any additional locking devices. By simply rotating the screws 230 90° after mounting the plate 210 upon the screws 230, the plate 210 is able to be locked onto the screw heads 236, with the grooves 242 achieving an interference fit with the notched region 222 of the flaps 220.

Anterior bone plate system 200 can be configured such that the bone screws 230 are capable of sliding with respect to the apertures 212 of the plate 210, until the screws 230 are properly seated and locked. Once locked, the anterior bone plate system allows for subsidence and micromotion to promote healing and fusion, while preventing extension. In order for the locking system to be implemented, bone plate 210 and channel 218 should be sized and configured to allow the oblong screw heads 236 sufficient room to rotate within the channel 218.

Bone plate 210 can contain at least two apertures 212 for allowing the screw heads 236 to pass through the plate 210. The apertures 212 should be positioned on the bone plate 21 0 such that the plate can attach to an upper and lower vertebral body. According to one aspect of the invention, the bone plate 210 can include modified T-slots fabricated thereon extending from one end of the plate 21 0 and directed longitudinally to the opposite end. The T-slots can include one elliptical slot extending vertically, and another slot extending horizontally. Lobes can be featured on the T-slots to provide interference with the ramps 240. By rotating the bone screw 230 90°, the screw head ramp interferes with the T-slots of the plate 210. Continued rotation allows the screws 230 to cam until the interference is cleared on the other side and the bone plate 210 is locked onto the screws 230.

Figure 7:
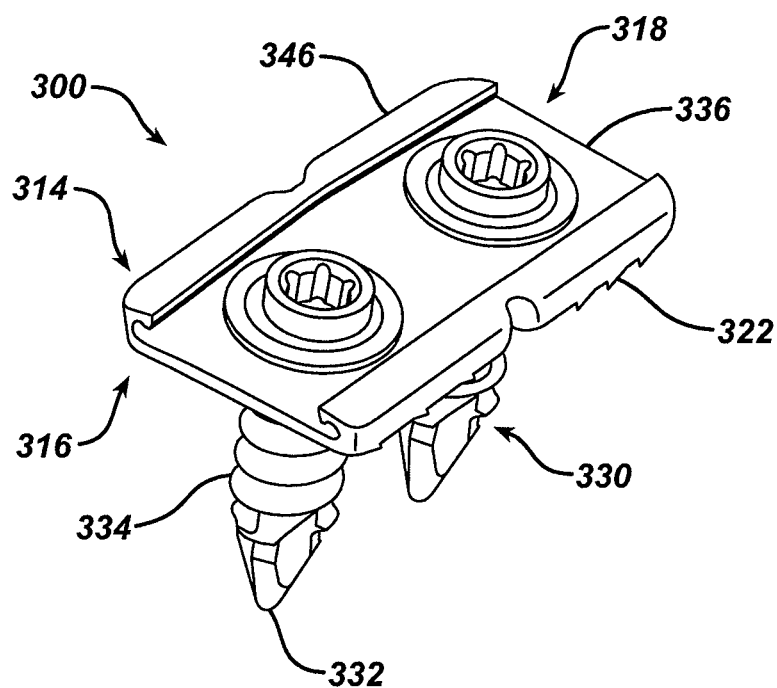
FIG. 7 is a perspective view of yet another embodiment of the anterior bone plate system of the present invention, wherein the screws are extending through the bone plate.
Figure 8:
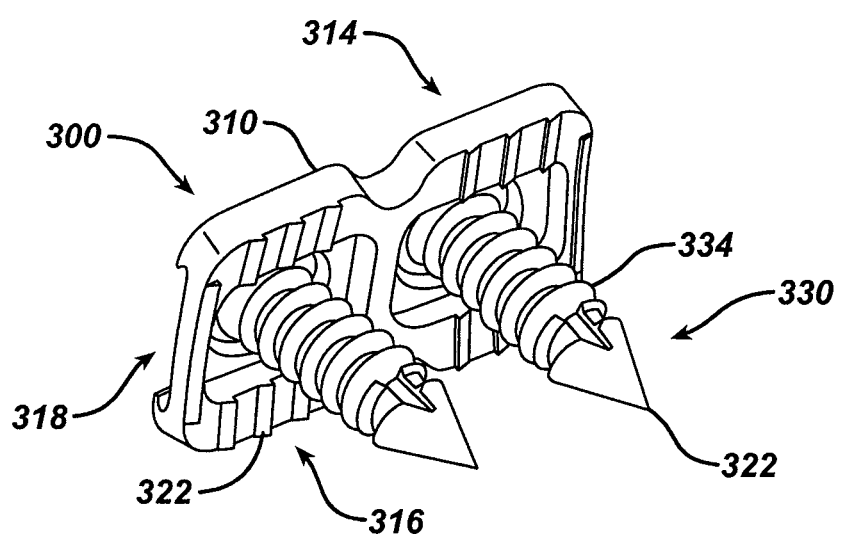
FIG. 8 is a perspective view showing the bottom of the system of FIG. 7.

In yet another exemplary embodiment of the present invention, anterior bone plate system 300 is shown in FIGS. 7 and 8. Bone plate system 300 includes bone plate 310 which has at least two apertures 312 extending from a first side 314 of the plate 310 that is configured to face away from bony structure to a second side 316 that is configured to contact bony surface. A channel 318 extends lengthwise down the first side 314 of the bone plate 310.

Consistent with anterior bone plate systems 100 and 200, the apertures 312 of bone plate 310 allow the plate 310 to be placed on top of previously positioned bone screws 330. Each bone screw 330 can have a self-tapping distal end 332 and a lower threaded portion 334 with an aggressive thread pitch to facilitate its purchase into bone. As shown in FIG. 8, each screw 330 includes a screw head 336 at an opposite (proximal) end that is adapted to seat within the channel 218. The major thread diameter of the lower threaded portion of the screws 330 can be in the range of about 3.5 to 5.5 mm, while the cancellous thread pitch of the lower threaded region 334 can be approximately 1.5 or more to provide unicortical purchase into bone. The bone screws 330 are placed in the midline of the vertebral body, with only one bone screw 330 per vertebral body or level required to adequately stabilize the bony segments to the plate 310 to reduce the amount of bone damage that would occur to the spine when more than one screw is inserted within the same vertebral body.

Bone plate 310 can also include surface features 322 such as cleats or ridges on the second side 316 that is adapted to contact bony surface as illustrated in FIG. 7. The surface features 322 help anchor the bone plate 310 onto the bony surface of the vertebral bodies yet still allow flexion or subsidence while preventing extension, which is undesirable for proper fusion and healing.

Figure 9:
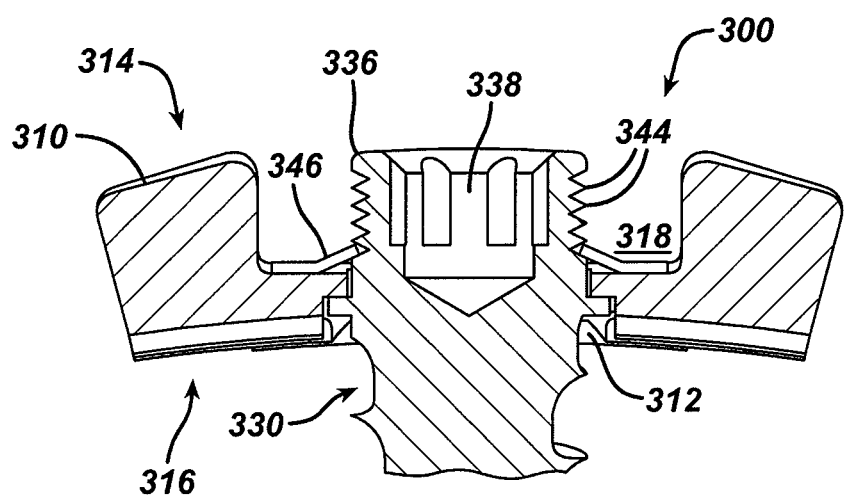
FIG. 9 is a cross-sectional view of the anterior bone plate system of FIG. 7.
Figure 10:
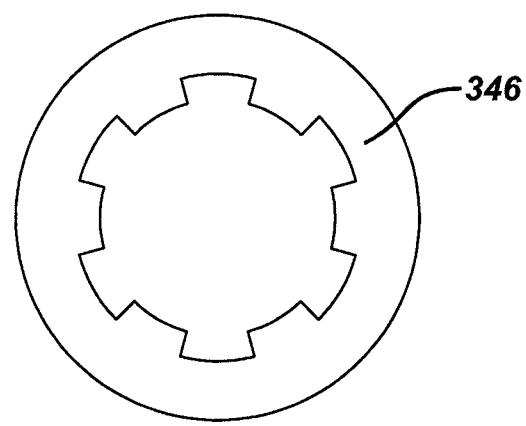
FIG. 10 is a detailed view of the retaining ring present in the system of FIGS. 7 and 9.

As shown in FIG. 9, each of the screws 330 can have an open head 336, which can include a shaped bore 338 for attachment to an inserter tool or screwdriver (not shown). Each screw head 336 can also include circumferential grooves 344 machined on the outside diameter of the screw head 336. The grooves 344 are set proud, i.e., not engaged in bone, for engaging a locking device such as retaining ring 346 as shown in FIG. 10. The channel 318 of the bone plate 310 is machined to provide a low profile that can accommodate the screw heads 336 and provide an overall consistently low profile, as illustrated in FIG. 9. Further, retaining rings 346 provide easy fastening between the bone screws 330 and the bone plate 310 without increasing the profile of the anterior bone plate system 300. While a retaining ring 346 of the shape shown in FIG. 10 is suitable, it is contemplated that the retaining ring can be configured in any number of geometries which would allow the retaining ring to be placed over the screw head 336 and against the bone plate 310.

Bone plate 310 can have at least two apertures 312. The apertures 312 can comprise two slots to enable the plate 310 to glide with respect to the screws 330. Alternatively, the apertures 312 can be a slot and a hole, or any configuration of a slot and hole that enables the screw head 336 to be passed through the plate 310, and which is configured to fix at least an upper and lower vertebral body.

In each of the anterior bone plate systems 100, 200, 300 described above, the bone plate 110, 210, 310 can be constructed so as to conform to the shape of the anterior surfaces of the vertebrae that it will be mounted upon. The plate can be curved along both its longitudinal and transverse axes such that the second side 116, 216, 316 is substantially concave to improve its conformity to the shape of the vertebral bodies. Further, one of ordinary skill in the art will appreciate that the bone plates 110, 210, 310 of the invention can be made of a variety of high strength, biologically compatible materials that are preferably compatible with MRI techniques. Useful materials include polymers, composite reinforced polymers, and metals such as stainless steel, titanium and titanium alloys.

In an exemplary method for implementing the anterior bone plate systems 100, 200, 300 described above, several steps are necessary to prepare the patient for surgery and before the plate system 100, 200, 300 can be installed. As an initial matter, the patient should be placed in a supine position, with the spine stabilized appropriately. Next, the patient is prepped and draped in the usual manner. Using radiographic imaging, the affected spinal level(s) or area(s) are identified. An incision is then made to optimize the exposure appropriate for the procedure.

Where necessary, decompression and grafting procedures are performed. To effect the decompression and grafting procedure, a distraction pin insertion instrument is used. The distraction pin insertion instrument allows distraction pins (also called Caspar pins) to be inserted perpendicular to the bone's anterior cortical surface or vertebral body, and perpendicular to the superior/inferior midline of the vertebral bodies. In the present invention, each vertebral body has only a single pin inserted. It is important to note that the pilot holes must be perfectly aligned, i.e., distraction pins must be inserted perfectly parallel. Routine distraction is then performed and a diskectomy, the surgical removal of a diseased disc, follows. A graft can then be placed into the evacuated disc space under gentle distraction and when the surgeon is comfortable with placement, the distraction instrument and Caspar pins are removed.

The bone screws 130, 230, 330 of the present invention are preferably inserted into pilot holes left in the vertebral bodies or bony segments that will be attached to the bone plate 110, 210, 310 by the Caspar pins. It is also possible to drill using about a 2.0 mm diameter drill bit prior to using the distraction pins. The distraction procedure provides each vertebral body with a pilot screw hole for placement of a bone screw 130, 230, 330. It should be noted that, while the bone screws are preferably used with pilot holes, it is possible to use the anterior bone plate systems 100, 200, 300 without pilot holes as well, i.e., without first using a distraction pin instrument.

After the pilot holes are prepared, all anterior anomalies, i.e., osteophytes, that can impede bone plate 110, 210, 310 placement are removed. Using an osteophyte remover instrument, the endplate and anterior column of the vertebral body is prepared to allow the underside of the plate 110, 210, 310 to be sandwiched tightly against the vertebral bodies to promote osseous fusion. The osteophyte remover instrument is used to create a smooth flat surface to fit the plate 110, 210, 310 precisely and match the plate's width. By shaving the vertebral bodies in this manner, the bone plate 110, 210, 310 is able to be inserted flush against the bony surface and produce a low profile which reduces the amount of damage to surrounding soft tissue.

Self-tapping screws 130, 230, 330 of the present invention are inserted into Caspar pinholes and tightened down to the anterior cortex, and aligned such that the open screw heads 136, 236, 336 are pointed so the openings are in the sagittal plane. The appropriate length plate 110, 210, 310 is then chosen by the surgeon and dropped onto the screw heads 136, 236, 336. The plate 110, 210, 310 is then secured down in the manner described above for bone plate systems 110, 210, 310 and finally the patient is closed in a standard manner.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A bone plate system comprising:
a bone plate having a first surface, a second bone contacting surface opposed to the first surface, and a plurality of oblong apertures extending through the bone plate, all of the apertures being aligned lengthwise along a centerline of the bone plate such that a midpoint of each aperture is positioned on the centerline of the bone plate;
a plurality of bone screws each having a head and a shank extending distally therefrom, the heads of the bone screws being disposable through the plurality of oblong apertures in the bone plate from a location distal to the second bone contacting surface and through the oblong apertures in a proximal direction toward the first surface, and the shanks being capable of insertion into bone to fasten the bone plate to bone;
wherein the bone plate is configured to slide along the centerline with respect to the plurality bone screws when the bone screws are disposed through the oblong apertures and fully inserted into bone to secure the bone plate to bone; and
wherein each of the bone screws is configured to be secured to the bone plate without an external component to lock the bone screw to the bone plate.

2. The system of claim 1, wherein the oblong apertures have major axes aligned with the centerline of the plate.

3. The system of claim 1, wherein the heads of the bones screws are formed thereon and have the shanks extending distally therefrom.

4. A bone plate system comprising:
a bone plate having a first surface, a second bone contacting surface opposed to the first surface, and a plurality of oblong apertures extending through the first and second surfaces of the bone plate, all of the apertures being aligned lengthwise along a centerline of the bone plate such that a central axis of each aperture intersects the centerline of the bone plate; and
a plurality of bone screws each having a head formed thereon and a shank extending distally from the head, each head being capable of insertion through the oblong apertures and each shank being capable of insertion into bone to fasten the bone plate to bone, the heads of the bone screws each having a maximum diameter greater than a maximum width of the apertures, the maximum width being measured transverse to the centerline;
wherein the bone plate is capable of moving along the centerline with respect to the plurality of bone screws when the bone screws are inserted through the oblong apertures and fully inserted into bone.

5. The system of claim 4, wherein the oblong apertures have major axes aligned with the centerline of plate.

6. The system of claim 4, wherein the heads of the bone screws are each configured to be disposable through the plurality of oblong apertures in the bone plate from a location distal to the second bone contacting surface and through the oblong apertures in a proximal direction toward the first surface.

7. The system of claim 4, wherein the heads of the bones screws each have a minimum diameter less than the maximum width of the apertures.

8. The system of claim 4, wherein the heads of the bone screws each have an oblong shape such that when the bone screws are inserted through the oblong apertures and the heads are each in a first position relative to the bone plate, the heads can be inserted through the oblong apertures, and when the bone screws are inserted through the oblong apertures and the heads are each in a second position relative to the bone plate, the heads cannot be inserted through the oblong apertures, the second position being rotated from the first position.

9. The system of claim 8, wherein the second position is rotated 90° from the first position.

10. The system of claim 4, wherein each of the bone screws is configured to be secured to the bone plate without an external component to lock the bone screw to the bone plate.

* * * * *